US010478279B2

(12) United States Patent
Bowley et al.

(10) Patent No.: US 10,478,279 B2
(45) Date of Patent: Nov. 19, 2019

(54) IMPLANTABLE PROSTHETIC DEVICE

(71) Applicant: C.R. Bard, Inc., Murray Hill, NJ (US)

(72) Inventors: Melissa Bowley, Newport, RI (US); Brian Leach, Hope, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 309 days.

(21) Appl. No.: 15/257,971

(22) Filed: Sep. 7, 2016

(65) Prior Publication Data

US 2018/0064521 A1 Mar. 8, 2018

(51) Int. Cl.
*A61F 2/02* (2006.01)
*A61F 2/00* (2006.01)

(52) U.S. Cl.
CPC .... *A61F 2/0063* (2013.01); *A61F 2002/0068* (2013.01); *A61F 2250/0023* (2013.01); *A61F 2250/0036* (2013.01); *A61F 2250/0039* (2013.01)

(58) Field of Classification Search
CPC .................. A61F 2/0063; A61F 2/0077; A61F 2002/0068; A61F 2002/0086; A61F 2250/0023; A61F 2250/0036; A61F 2250/0039
See application file for complete search history.

(56) References Cited

U.S. PATENT DOCUMENTS

| 5,954,767 | A | 9/1999 | Pajotin et al. |
|---|---|---|---|
| 6,368,541 | B1 | 4/2002 | Pajotin et al. |
| 6,669,735 | B1 | 12/2003 | Pelissier |
| 7,404,819 | B1 * | 7/2008 | Darios ............... A61F 2/0063 606/151 |
| 8,182,545 | B2 | 5/2012 | Cherok et al. |
| 2003/0130745 | A1 | 7/2003 | Cherok et al. |
| 2003/0212460 | A1 | 11/2003 | Darois et al. |
| 2011/0015760 | A1 | 1/2011 | Kullas |
| 2015/0088168 | A1 | 3/2015 | Hamlin et al. |

FOREIGN PATENT DOCUMENTS

| WO | WO 2012/040193 A1 | 3/2012 |
|---|---|---|
| WO | WO 2016/105415 A1 | 6/2016 |

OTHER PUBLICATIONS

International Search Report and Written Opinion for International Application No. PCT/US2017/050280, dated Nov. 6, 2017.

\* cited by examiner

*Primary Examiner* — Melanie R Tyson
(74) *Attorney, Agent, or Firm* — Wolf, Greenfield & Sacks, P.C.

(57) ABSTRACT

An implantable prosthesis and a method of repairing an anatomical defect, such as a soft tissue defect, by promoting tissue growth with the prosthetic. The prosthesis includes a body with an inner portion and an outer margin that extends outwardly beyond the inner portion, the outer margin including an inner portion side and an outer peripheral edge. The outer margin includes a tissue infiltratable portion, such as a tissue infiltratable layer, having a thickness that decreases from the inner portion side towards the outer peripheral edge.

34 Claims, 8 Drawing Sheets

IMPLANTABLE PROSTHETIC DEVICE

FIELD

The present invention relates to an implantable prosthesis and, more particularly, to a prosthesis for use in soft tissue repair and reconstruction.

BACKGROUND

Various prosthetic devices have been proposed to repair and reinforce anatomical defects, such as tissue and muscle wall hernias. For example, ventral and inguinal hernias are commonly repaired using a sheet of biocompatible fabric, such as a knitted polypropylene mesh (BARD MESH). The fabric is typically sutured, stapled or otherwise provisionally anchored in place over, under or within the defect. Tissue integration with the fabric, such as by tissue ingrowth into and/or along the fabric, eventually completes the repair.

SUMMARY

According to one embodiment, an implantable prosthesis for repairing a soft tissue defect is disclosed. The implantable prosthesis includes a body configured to cover or plug the soft tissue defect, the body having an inner portion and an outer margin extending outwardly beyond the inner portion, the outer margin having an inner portion side and an outer peripheral edge. The outer margin includes a tissue infiltratable portion having a thickness that decreases in an outwardly direction from the inner portion side towards the outer peripheral edge.

According to another embodiment, an implantable prosthesis for repairing a soft tissue defect is disclosed. The implantable prosthesis includes a body configured to cover or plug the soft tissue defect, the body having an inner portion and an outer margin extending outwardly beyond the inner portion, the outer margin having an inner portion side and an outer peripheral edge. The inner portion includes a knitted fabric with a first pore size and the outer margin includes a knitted fabric with a second pore size, the second pore size being greater than the first pores size.

According to still another embodiment, an implantable prosthesis for repairing a soft tissue defect is disclosed. The implantable prosthesis includes a body configured to cover or plug the soft tissue defect, the body having an inner portion and an outer margin extending outwardly beyond the inner portion, the outer margin having an inner portion side and an outer peripheral edge. The outer margin includes a tissue infiltratable portion, wherein a rate of tissue resorption of the tissue infiltratable portion decreases in a direction away from the outer peripheral edge towards the inner portion side.

According to yet another embodiment, a method of repairing a soft tissue defect with an implantable prosthesis is disclosed. The method includes covering or plugging the soft tissue defect with the implantable prosthesis, the prosthesis including a body having an inner portion and an outer margin extending outwardly beyond the inner portion, the outer margin having an inner portion side and an outer peripheral edge. The outer margin includes a tissue infiltratable portion having a thickness that decreases in an outwardly direction from the inner portion side towards the outer peripheral edge.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF INVENTION

Figure 1:
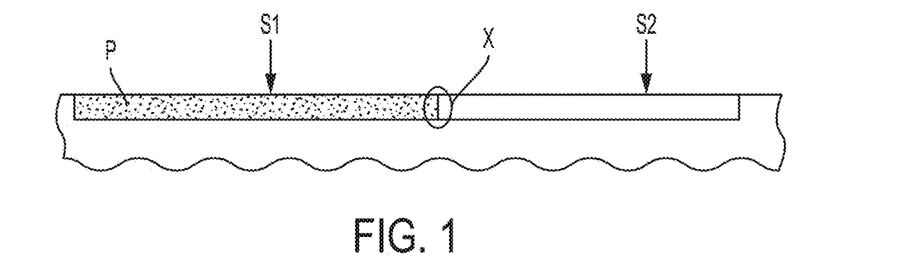
FIG. 1 is a cross-sectional schematic representation of a typical implantable prosthesis with tissue integration.

Implantable prostheses are used for repairing soft tissue defects, such as ventral and inguinal hernias, and/or in chest wall reconstruction, by promoting tissue integration with the implantable prosthetic, such as by tissue ingrowth. Traditional prostheses, such as that shown in FIG. 1 (see, e.g., the prosthesis labeled P) may prevent or limit mobility of the integrated tissue. For example, in some instances, the strain rate S1 of such infiltrated tissue may be low (e.g., at or near 0%) in certain postoperative patients. Assuming that the strain rate S2 of the native tissue (e.g., the non-infiltrated tissue) is about 100%, the interface X between the infiltrated tissue and native tissue may experience high stresses.

Figure 2:
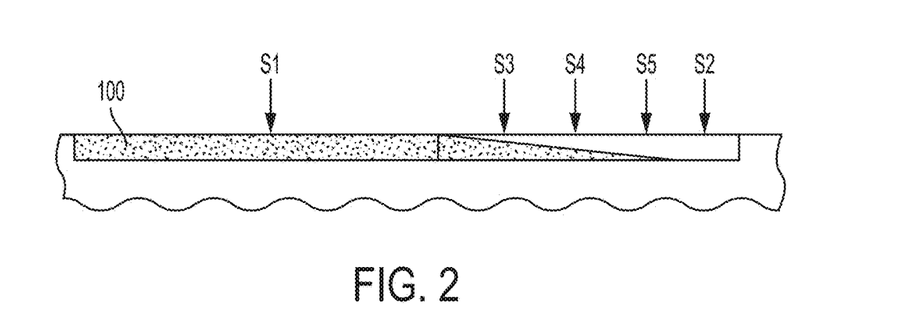
FIG. 2 is a cross-sectional schematic representation of an implantable prosthesis with tissue integration according to one embodiment of the current disclosure.

Applicant has realized that by increasing the strain rate of the regions of the infiltrated tissue and by reducing or eliminating the high stress interfaces, various advantages may be realized. To that end, embodiments disclosed herein comprise an implantable prosthesis with a body having a tissue infiltratable portion that decreases in thickness in an outwardly direction (e.g., in a direction towards an outer peripheral edge of the prosthesis body). For purposes herein, a tissue infiltratable portion may include a tissue infiltratable fabric that permits tissue ingrowth to enhance the repair of the defect. In some embodiments, such as that shown in FIG. 2, the prosthesis body includes a tissue infiltratable layer having a thickness that decreases in the outwardly direction. In such embodiments, the strain rate of the infiltrated tissue may increase to about 100% (e.g., from the arrow labelled S1 to the arrow labelled S2). In some embodiments, a tissue infiltratable layer of repair fabric may create a gradual increase in the strain rates of the infiltrated tissue, with intermediate strain rates of about 25%, 50%, and 75%, for example (see the arrows labelled S3, S4, S5, respectively).

Embodiment disclosed herein also comprise an implantable prosthesis with a body having a tissue infiltratable portion, such as a tissue infiltratable layer, with a rate of tissue resorption that decreases in an inwardly direction (e.g., in a direction away from the outer peripheral edge). For example, in some embodiments, the rate of resorption of an outer margin of the prosthesis may be greater than the rate of an inner portion for tissue growth. In some embodiments, such a decreased rate may be achieved by decreasing the thickness of the tissue infiltratable layer in the outwardly direction.

According to one aspect, the prosthesis includes a body having an inner portion and an outer margin extending outwardly beyond the inner portion. The outer margin may include an inner portion side, adjacent to the inner portion, and an outer peripheral edge. In some embodiments, the body includes a tissue infiltratable portion, such as a tissue infiltratable layer, having a thickness that decreases in an outwardly direction. For example, the outer margin may include a tissue infiltratable portion having a thickness that decreases from the inner portion side towards the outer peripheral edge.

As will be appreciated, the entire body need not be tissue infiltratable. For example, in some embodiments, the inner portion may be less or non-tissue infiltratable, with only a portion of the outer margin being tissue infiltratable. In some embodiments, the inner portion is less or non-tissue infiltratable while the outer margin is tissue infiltratable. In such embodiments, the thickness of the tissue infiltratable layer, such as the thickness of the outer margin, may decrease in an outwardly direction from the inner portion side to the outer peripheral edge. For example, a thickness of a first portion of the outer margin may be greater than a thickness of a second portion of the outer margin, the second portion being closer to the outer peripheral edge than the first portion.

In other embodiments, the entire body may be tissue infiltratable. In such embodiments, a tissue infiltratable layer may be formed such that a thickness of the outer margin is less than a thickness of the inner portion. As with previous embodiments, the tissue infiltratable layer also may be formed such that the thickness of the outer margin decreases in the outwardly direction from the inner portion side to the outer peripheral edge. As will be appreciated, in these embodiments, irrespective of whether the outer margin, and possibly the inner portion, has a decreasing thicknesses, the entire body (up to and including the outer peripheral edge of the tissue infiltratable layer) may be configured to allow tissue ingrowth.

Figure 3:
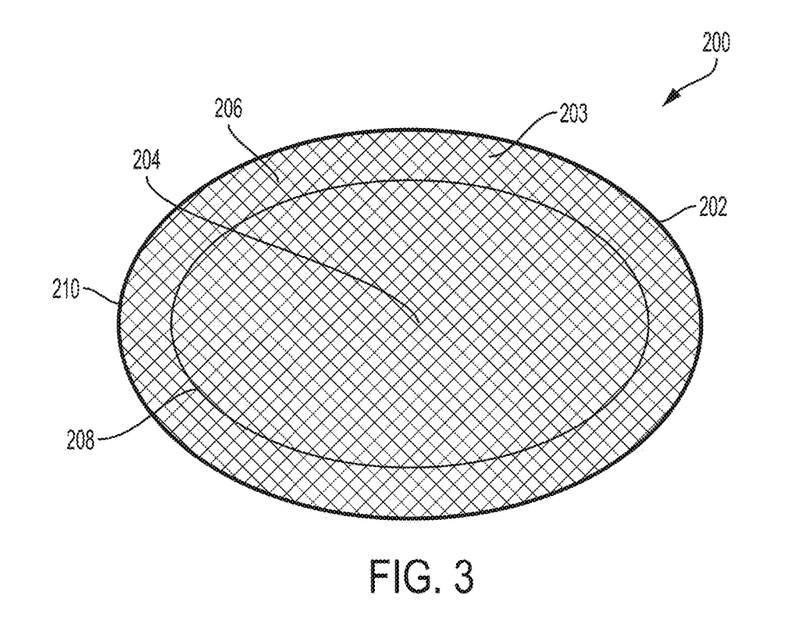
FIG. 3 is a schematic top view of an implantable prosthesis according to another embodiment.

Turning now to the figures, FIG. 3 shows a prosthesis 200 according to one aspect of the present disclosure. As shown in this figure, the prosthesis 200 includes a body 202 with an inner portion 204 and an outer margin 206, the outer margin 206 extending outwardly beyond the inner portion 204. In some embodiments, the outer margin 206 includes an inner portion side 208, adjacent to the inner portion 204, and an outer peripheral edge 210. In some embodiments, the outer margin is more flexible than the inner portion.

In some embodiments, the body 202 includes a tissue infiltratable portion, such as tissue infiltratable layer 203. In one embodiment, as shown in FIG. 3, both the inner portion 204 and the outer margin 206 include the tissue infiltratable layer 203. As will be appreciated, in other embodiments, only the outer margin may include the tissue infiltratable layer.

Figure 4A:
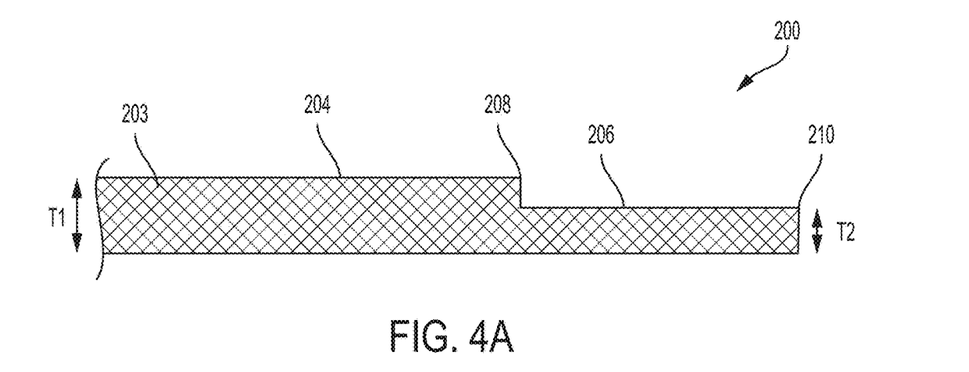
FIGS. 4A-4C are cross-sectional schematic side views of implantable prostheses according to several illustrative embodiments.
Figure 4B:
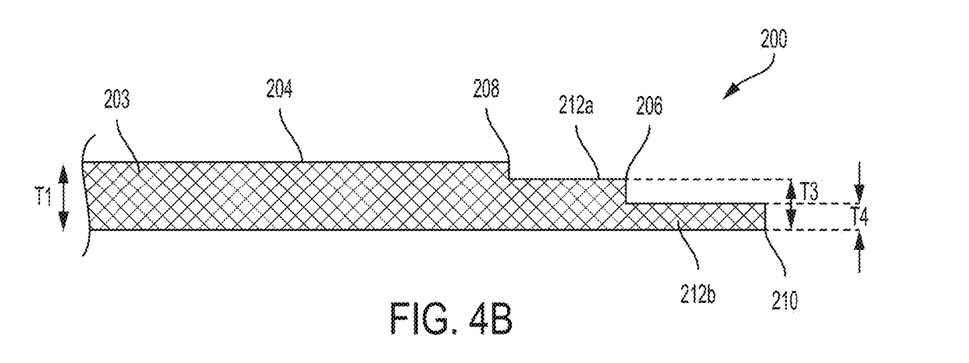
Figure 4C:
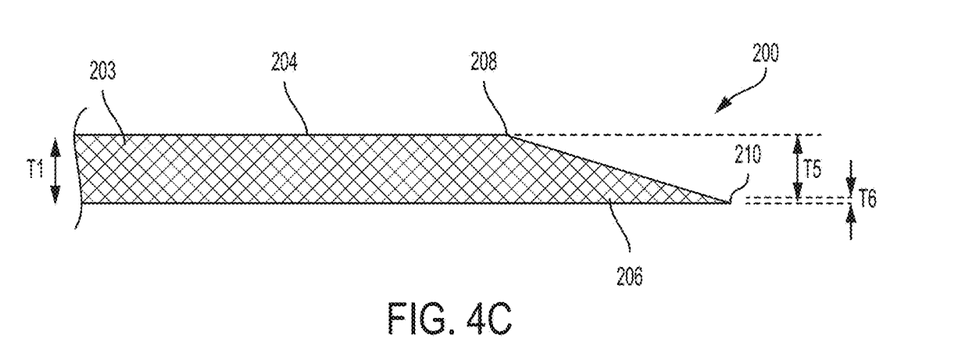

As illustrated in FIGS. 4A-4C, according to one aspect, the tissue infiltratable layer 203 has a thickness that decreases in the outwardly direction, such as from the inner portion 204 towards the outer peripheral edge 210. For example, the thickness of the outer margin 206 may decrease from the inner portion side 208 towards the outer peripheral edge 210. As will be appreciated, although the inner portion 204 is shown as being tissue infiltratable in these figures, the inner portion 204 also may be less tissue infiltratable than the outer margin or non-tissue infiltratable.

In some embodiments, as shown in FIG. 4A the tissue infiltratable layer is formed such that the inner portion 204 has a thickness T1 that is greater than a thickness T2 of the outer margin 206. In such embodiments, the thicknesses of the inner portion and outer margin may be uniform across each respective section. In some embodiments, the ratio between the thickness T2 of the outer margin 206 and the thickness T1 of the inner portion 204 (T2/T1) is less than about 1. For example, in some embodiments, the ratio T2/T1 between the thicknesses of the outer margin 206 and inner region 204 is between about 0.25 and 0.75, although the ratio may vary in other embodiments.

Without wishing to be bound by theory, the ratio of the decrease in thickness of the tissue infiltratable layer may lead to a respective increase in the strain rate of the infiltrated tissue. For example, in some embodiments, there may be an inverse relationship between the decrease in thickness and the increase in strain rate. In one such embodiment, where the ratio between the thicknesses of the outer margin and the inner portion is about 0.25, the strain rate increase may be about 75%.

As shown in FIG. 4B, in other embodiments, the tissue infiltratable layer is formed such that the thickness of the outer margin decreases in a stepped fashion. For example, the outer margin may have a first thickness T3 extending over a first portion or step 212a and a second thickness T4 extending over a second portion or step 212b. As shown in this figure, the second portion 212b is located outwardly of the first portion 212a. In such embodiments, the first and second thicknesses T3, T4, and the sum of the first and second thicknesses, is less than the thickness T1 of the inner portion 204. As will be appreciated, the thickness T3, T4 of each step may be the same in some embodiments, although the thicknesses T3, T4 also may differ.

Although the outer margin 206 is shown as having two steps in FIG. 4B, the tissue infiltratable layer 203 may have more steps in other embodiments (e.g., three or more steps). As will be appreciated, the length of each step may be the same in some embodiments, although the steps also may have different lengths.

In some embodiments, as shown in FIG. 4C, the thickness of the outer margin may decrease progressively from the inner portion side 208 towards the outer peripheral edge 210. For example, the thickness of the outer margin may gradually decrease from a first thickness T5 at the inner portion side 208 to a second thickness T6 at the outer peripheral edge 210. As will be appreciated, the first thickness T5 may be the same or substantially the same as the thickness T1 of the inner portion 204. These thicknesses also may differ, with the first thickness T5 being less than the thickness T1 of the inner portion 204. In some embodiments, the second thickness T6 may approach zero (e.g., may be about 0.01 inches).

Although the outer margin is shown as having a consistent type of thickness decrease (e.g., a gradual decrease or a stepped decrease), in some embodiments, the outer margin may have more than one type of thickness decreases. For example, the outer margin may have a first step with a uniform thickness and a second step with a thickness that gradually decreases.

As shown and described in the above embodiments, the thickness of the tissue infiltratable portion may decrease from the inner portion towards the outer peripheral edge. In such embodiments, the thickness of the body, such as the thickness of the outer margin, may decrease between about 5% and 100%. For example, in an embodiment in which the outer margin is tissue infiltratable, the thickness of the outer margin may decreases between about 5% and 100% between the inner portion side and the outer peripheral edge. The thickness of the outer margin also may decrease between about 50% and 90% between the inner portion side and the outer peripheral edge.

In some embodiments, the outer margin may progressively decrease between about 5% and 100%. For example, as shown in FIG. 4C, the thickness of the outer margin may decrease gradually from a first thickness to a second thickness that is 5% of the first thickness. As shown in FIG. 4B, in other embodiments, the thickness of the outer margin may decrease in steps. For example, the outer margin may decrease from a first thickness to a second thickness that is 50% of the first thickness, and then to a third thickness that is 25% of the first thickness. As will be appreciated, the thickness of the outer margin (or other portions of the body) also may decrease according to other profiles.

Figure 5:
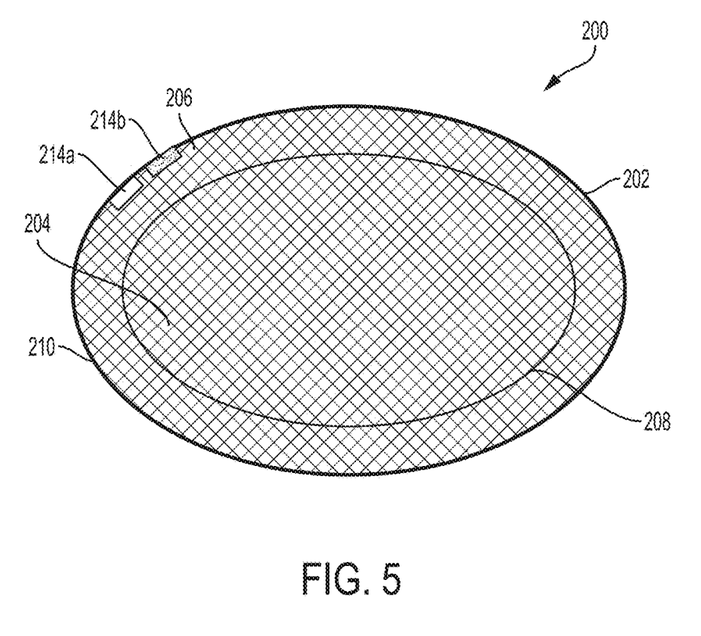
FIG. 5 is a top view of an implantable prosthesis according to another embodiment.

As shown and described in FIGS. 4A-4C, the thickness of the tissue infiltratable layer may decrease in an outwardly direction. In such embodiments, the thickness may still be uniform in a peripheral (e.g., circumferential) direction. For example, the tissue infiltratable layer may have the same thickness at the second step all the way around the prosthesis body (e.g., all the way around the outer margin). In other embodiments, as shown in FIG. 5, the thickness of the tissue infiltratable layer may be non-uniform along the peripheral direction. For example, a thickness of a first portion 214a of the outer margin 206 (e.g., a first portion of the outer peripheral edge) may be different than a thickness of a second portion 214b of the outer margin 210 (e.g., a second portion of the outer peripheral edge). As will be appreciated, this may allow the increase in strain rates to be changed (e.g., to be increased) not just in the outwardly directly but also in the peripheral direction.

As shown in FIG. 5, the first and second outer margin portions 214a, 214b may be spaced apart from one another in some embodiments, although the outer margin portions 214a, 214b also may be adjacent to each other. In embodiments in which the outer margin portions are spaced apart from one another, a tissue infiltratable portion may be located in between the outer margin portions. Such a tissue infiltratable layer may include a decreasing thickness in the outwardly direction, but not in the peripheral direction.

Although the entire body is shown as being tissue infiltratable in FIG. 5, in other embodiments, only a portion or none of the prosthesis body may be tissue infiltratable. For example, only the first and second outer margin portions 214a, 214b may be tissue infiltratable, with the rest of the prosthesis body being less tissue infiltratable than either of the first or second outer margin portions 214a, 214b or non-tissue infiltratable. In such embodiments, as will be appreciated, the outer margin may include additional portions that are also tissue infiltratable, such as third, fourth and fifth outer margin portions with varying thicknesses in the outwardly and peripheral directions.

According to another aspect, the body 202 of the prosthesis 200 is configured to cover or plug the tissue or muscle wall defect. In some embodiments, the prosthesis may have a length along a major axis A of between about 5 inches and 6.5 inches. In such embodiments, the prosthesis may have a width along a minor axis B of between about 3 inches and 4.5 inches. As will be appreciated, the prosthesis may have other sizes suitable for covering (or plugging) a defect.

Figure 6:
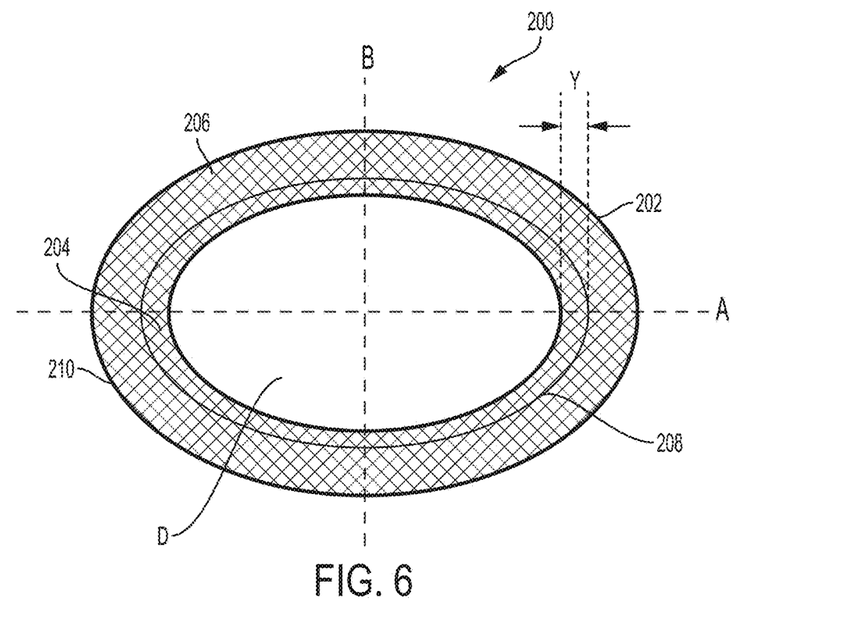
FIG. 6 is a top view of an implantable prosthesis adjacent a soft tissue defect.

In some embodiments, as shown in FIG. 6, the body 202 is sized such that only the inner portion 204 of the prosthesis 200 covers the defect D. For example, in some embodiments, the inner portion 204 of the body 202 is sized such that the inner portion 204 extends between about 3 cm and 5 cm beyond the defect D when the prosthesis 200 is placed over the defect D (see, e.g., the distance Y between an outer edge of the defect D and an outer edge of the inner portion 204). As will be appreciated, the body 202 also may be sized such that the inner portion 204 and at least a portion of the outer margin 206 covers the defect D. In such an embodiment, the portion of the outer margin 204 covering the defect D may have a decreasing thickness.

As will be appreciated, the prosthesis may be configured to have any suitable shape or size that is conducive to facilitate mending of the particular defect D. In the embodiments shown in FIG. 6, the prosthesis has a relatively flat configuration. However, the prosthesis need not be flat. For example, convex, concave, convex/concave, and more complex three-dimensional shapes also are contemplated. As with other embodiments, in such non-flat configurations, the thickness of the prosthesis body may still decrease in the outwardly direction. In some embodiments, the prosthesis may be sufficiently pliable to facilitate manipulation and/or reduction of the prosthesis during delivery to the defect and/or to conform the prosthesis to the anatomical site of interest.

Figure 7:
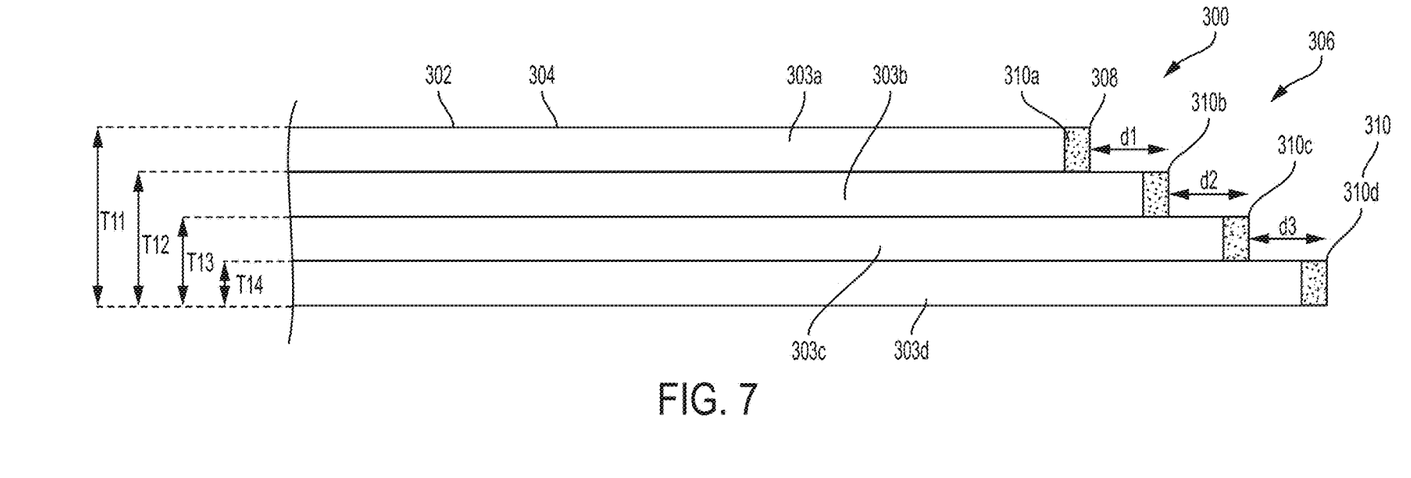
FIG. 7 is a cross-sectional schematic side view of an implantable prosthesis according to another embodiment.

Although the prostheses 200 of FIGS. 3-6 include a body 202 with only one tissue infiltratable layer 203, according to another aspect, the prosthesis body may include two or more tissue infiltratable layers. For example, as shown in FIG. 7, the prosthesis body 302 may include first, second, third and fourth tissue infiltratable layers 303a, 303b, 303c, 303d having corresponding first, second, third, and fourth outer peripheral edges 310a, 310b, 310c, 301d, respectively. As will be appreciated, multiple layers of tissue infiltratable fabric may enhance or influence various properties of the prosthesis. In such embodiments, any one or combination of the layers may be formed of any biologically compatible material, suitable for repairing a soft tissue defect.

As shown in FIG. 7, in embodiments having two or more tissue infiltratable layers, the prosthesis body 302 includes an inner portion 304 and an outer margin 306, the outer margin having an inner portion side 308, adjacent to the inner portion, and an outer peripheral edge 310. In one such embodiment, a first outer peripheral edge 310a coincides with the inner portion side 308 and a fourth outer peripheral edge 310d coincides with the outer peripheral edge 310 of the body 302.

In some embodiments, the four layers 303a, 303b, 303c, 303d are stacked one on top of another such that the smallest layer 303a is positioned at the top of the body 302 and the largest layer 303d is positioned at the bottom of the body 302. In such an arrangement, when the layers 303a, 303b, 303c, 303d are stacked on top of one another, the first outer peripheral edge 310a is positioned inwardly of the second outer peripheral edge 310b, which is positioned inwardly of the third outer peripheral edge 310c, which is positioned inwardly of the fourth outer peripheral edge 301d. As will be described, such an arrangement results in an overall thickness of the outer margin decreasing towards the outer peripheral edge 310.

In some embodiments, the layers are positioned equally with respect to one another. For example, the distances (e.g., d1, d2, d3) between the outer peripheral edges of adjacent layers are equal. In such embodiments, as will be appreciated, the first layer 303a may be centered on the second layer 303b, which may be centered on the third layer 303c, which, in turn, may be centered on the fourth layer 303d. In other embodiments, the distances between the outer peripheral edges of the adjacent layers also may be different, such that two or more of the layers are not centered on one another.

As with other embodiments, the thickness of the outer margin 206 shown in FIG. 7 may decreases from the inner portion side 308 towards the outer peripheral edge 302. For example, the thickness of the outer margin 306 may decrease in a stepped fashion such that a first thickness T11 of the outer margin is greater than the second thickness T12, which is greater than the third thickness T13, which, in turn, is greater than the fourth thickness T14. In such embodiments, the size of each step corresponds to the distance between adjacent layers and the thickness of the outer margin at each step corresponds to a sum of the stacked layers at that step. For example, the first step, extending over distance d1 has a thickness T12 equal to the sum of thicknesses of the second, third, and fourth layers 303b, 303c, 303d. In a similar fashion, the second and third steps, extending over distances d2 and d3, have third and fourth thicknesses T13 and T14, respectively. The third thickness T13 equals a sum of thicknesses of the third and fourth layers 303c, 303d, and the fourth thickness T14 equals a thickness of the fourth layer 303d. As will be appreciated, the first thickness T11, extending from the inner portion 304 to the inner portion side 308 equals the sum of the thicknesses of all four layers 303a, 303b, 303c, 303d.

In some embodiments, the thicknesses of the first, second, third and fourth layers are the same, although the thickness of one layer also may be different from another layer. The thickness of a layer may be uniform across the layer, although it also may be non-uniform. For example, the thickness of one of the layers may decrease in an outwardly direction.

In the embodiments shown in FIGS. 4-7, the decreasing thickness of the outer margin may be achieved by physically modifying the tissue infiltratable portion. For example, the decreasing thickness may be achieved by physically removing a portion of the tissue infiltratable layer corresponding to the first step shown in FIG. 4C. The varying thickness also may be achieved by stacking and bonding layers together, as shown in FIG. 7. In still another embodiment, the decreasing thickness may be achieved by applying heat between two platens. For example, two platens that form a substantially triangular shape in the outer margin, like that in FIG. 4C, may be heated and pressed together to form the outer margin with the progressive thickness decrease.

Figure 8:
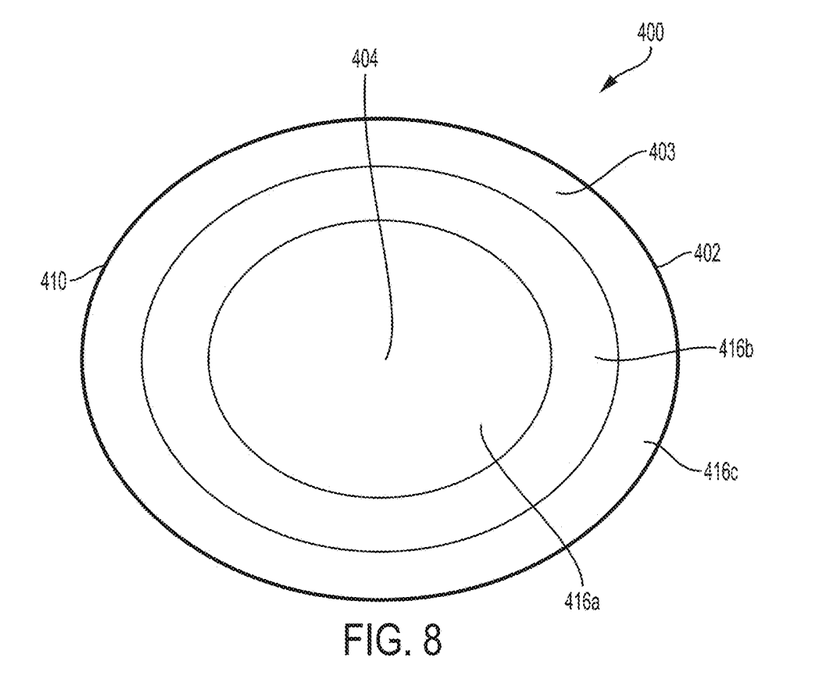
FIG. 8 is a schematic top view of an implantable prosthesis according to another embodiment.

In other embodiments, the decreasing thickness of the tissue infiltratable portion (e.g., the tissue infiltratable layer) may be achieved by varying the fabrics used to form the tissue infiltratable portion and/or by varying the characteristics of the fabrics. For example, as shown in FIG. 8, the body may include a tissue infiltratable layer 403 having three sections (e.g., three rings) 416a, 416b, 416c that are formed of two or more different fabrics and/or formed of two or more fabric(s) having different characteristics. As illustrated in this figure, the third section 416c extends outwardly beyond the second section 416b, which, in turn, extends outwardly beyond the first section 316a. In some embodiments, the body 402 also includes an outer peripheral edge 410 that extends outwardly beyond the third section 416c.

As will be appreciated, although three sections are shown in FIG. 8, the body may have more or fewer sections in other embodiments. For example, the body may include only two sections, or the body may include more than three sections. In some embodiments the first section 416a may include the inner portion 404 arranged to cover the defect. In some embodiments, the third section 416c may include the outer margin.

In some embodiment, the tissue infiltratable layer is formed of a knitted fabric with the first, second and third sections 416a, 416b, 416c formed of the knitted fabric with different pore sizes. For example, the first section, second, and third sections 416a, 416b, 416c may be formed of the knitted fabric with first, second and third pore sizes, respectively. In some embodiments, the pore size of the knitted fabric increases in an outwardly direction (e.g., towards the outer peripheral edge 410), with the first pore size being smaller than both the second and third pore sizes. In some embodiments, the knitted fabric is formed of monofilament or multifilament fibers. In some embodiments, the knitted fabric is a knitted mesh.

In other embodiments, the first, second and third sections 416a, 416b, 416c are formed of monofilament or multifilament fibers of different diameters. For example, the first, second and third sections 416a, 416b, 416c may be formed of monofilament or multifilament fibers of first, second and third diameters, respectively. In some embodiments, the diameter of the fibers decreases in an outwardly direction (e.g., towards the peripheral edge 410), with the first diameter being greater than the second diameter, which also may be greater than the third diameter.

In still another embodiment, the first, second and third sections may be formed of the knitted fabric having different knit patterns. For example, the first, second, and third sections 416a, 416b, 416c may be formed of the knitted fabric having first, second and third knit patterns, respectively. For example, the knit patterns may include a single knit, a double knit, a circular knit, or another suitable knit pattern. In such embodiments, the first knit pattern may differ from both the second and third knit patterns. As will be appreciated, the first knit pattern also may differ from only one of the other knit patterns (e.g., may differ from only the third knit pattern).

In other embodiments, the first, second and third sections 416a, 416b, 416c may be formed of fabric(s) having first, second and third fabric constructions, respectively. In some embodiments, the fabric constructions may include a knitted fabric, a woven fabric, a braided fabric, or another suitable fabric construction. As with other embodiments, the first, second, and third fabric constructions may differ from one another. The first fabric construction also may differ from only one of the other fabric constructions (e.g., may differ from only the second fabric construction). As will be appreciated, the first, second and third fabric constructions may be formed of the same fabric (e.g., a knit) or of more than one fabric (e.g., a knit and woven).

In some embodiments, the tissue infiltratable layer is formed by physically modifying the tissue infiltratable portion (e.g., as described with respect to FIGS. 3-7), and also by varying the fabrics types and/or fabric characteristics (e.g., diameter size, knit pattern, and construction). For example, the prosthesis body may have an outer margin with a thickness that decreases in steps (e.g., first, second, and third thicknesses at first, second and third steps, respectively), with each step being formed of a knitted fabric with different pore sizes. In another example, the prostheses body may have two or more tissue infiltratable layers, with each layer being formed of a fabric with a different fabric construction.

Although the prostheses shown and described are generally oval, elliptical or egg shaped, it will be appreciated that the bodies may have different shapes in other embodiments. For example, the prosthesis body may be circular, square, rectangular, or another suitable shape. Additionally, for prostheses having two or more fabric layers, the shape of the first layer need not be the same shape as that of the second layer. For example, the first layer may include an ovular shape, while the second layer may be rectangular.

In some embodiment, the tissue infiltratable portion has a thickness of between about 0.015 inches and 0.33 inches. For example, in some embodiments, the tissue infiltratable fabric may have a thickness of between about 0.015 inches and 0.1 inches. In such examples, when the repair fabric includes a monofilament or multifilament, the monofilament or multifilament may have a diameter of approximately 0.0043 inches.

In some embodiments, the tissue infiltratable portion may include one or more sheets of a prosthetic repair fabric. Such repair fabric may be formed of a biologically compatible, flexible repair material that includes a plurality of interstices or openings which allow sufficient tissue or muscle ingrowth to integrate the prosthesis with host tissue after implantation. In embodiments having multiple sheets of tissue infiltratable fabric, the multiple sheets may enhance the strength of the prosthesis and/or the amount of tissue ingrowth to the prosthesis. In such embodiments, the one or more sheets of prosthetic repair fabric may be bonded or otherwise joined together to form the tissue infiltratable portion. The one or more sheets may have the same or different thickness and may be made of the same or different materials. As will be appreciated, the prosthesis is not so limited, and one or more sheets may be formed of any biologically compatible material, synthetic or natural, suitable for repairing a tissue or muscle wall defect.

In some embodiments, the prosthetic repair fabric may include a polypropylene mesh which may promote rapid tissue or muscle ingrowth into and around the mesh structure. In such embodiments, varying the thickness of the mesh layer may impact scar plate formation, which may result in a more pliable tissue (e.g., a higher strain rate).

As will be appreciated, other surgical materials which are suitable for tissue or muscle reinforcement and defect correction also may be utilized, including BARD MESH (available from C.R. Bard, Inc.), SOFT TISSUE PATCH, SURGIPRO, TRELEX, PROLENE and MERSILENE, and other mesh materials. Resorbable materials, including polyglactin (VICRYL) and polyglycolic acid (DEXON), may be suitable for applications involving temporary correction of tissue or muscle defects. Collagen materials such as COOK SURGISIS also may be used.

Figure 9:
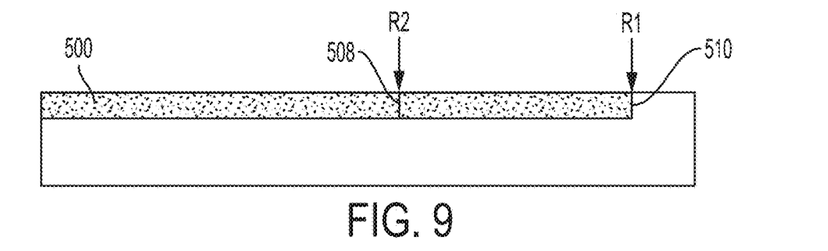
FIGS. 9 and 10 are schematic cross-sectional illustrations of implantable prostheses with different rates of tissue integration according to another embodiment.
Figure 10:
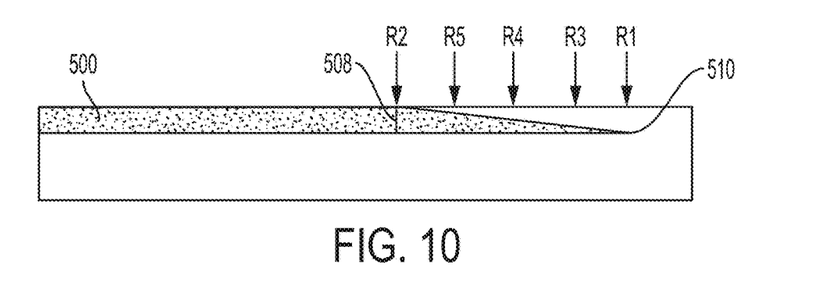

According to another aspect, the tissue infiltratable portion, such as the tissue infiltratable layer, may be configured such that a rate of tissue resorption decreases in an inwardly direction (e.g., from the outer peripheral edge towards the inner region of the prosthesis). For example, as shown in FIGS. 9 and 10, a rate of tissue resorption R1 at the outer peripheral edge 508 may be larger than a rate of tissue resorption R2 at the inner portion side 510. In such embodiments, the outer area may experience tissue resorption more quickly than tissue formation.

The prosthesis also may be configured such that the rate of tissue resorption gradually decreases from the outer peripheral edge 510 to the inner portion side 508. For example, intermediate rates of resorption (e.g., R3, R4, R5) at intermediate positions along the outer margin may be achieved. As shown in FIG. 10, the prosthesis 500 also may have a thickness that decreases in an outwardly direction (e.g., from the inner portion side 508 to the outer peripheral edge 510). As will be appreciated, the rate of resorption may be non-uniform across the layer, such as non-uniform in the peripheral direction.

According to another aspect, a method of repairing a soft tissue defect with an implantable prosthesis is disclosed. In some embodiments, the method includes covering or plugging the soft tissue defect with the implantable prosthesis. The prosthesis may include a body with an inner portion and an outer margin extending outwardly beyond the inner portion, the outer margin including an inner portion side and an outer peripheral edge. In some embodiments, the outer margin includes a tissue infiltratable portion with a thickness that decreases in the outwardly direction from the inner portion side towards the outer peripheral edge. The inner portion also may be tissue infiltratable.

In some embodiments, covering or plugging the soft tissue defect with the implantable prosthesis includes covering or plugging the defect with only the inner portion of the body. In such embodiments, the inner portion may extend between about 3 cm and 5 cm beyond the defect. In other embodiments, covering or plugging the soft tissue defect with the implantable prosthesis includes covering or plugging the defect with the inner portion of the body and at least a portion of the outer margin.

Although embodiments have been shown with a prosthesis used to cover or plug a soft tissue defect, it will be appreciated that such a prosthesis with a decreasing outer margin thickness or outer margin resorption may be used in other implants. For example, such a prosthesis may be used with another surgical implant, such as to anchor the surgical implant (e.g., a port) to a portion of the body.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An implantable prosthesis for repairing a soft tissue defect, the implantable prosthesis comprising:
a body configured to cover or plug the soft tissue defect, the body having an inner portion and an outer margin extending outwardly beyond the inner portion, the outer margin having an inner portion side and an outer peripheral edge, wherein the outer margin includes a tissue infiltratable portion having a thickness that decreases in an outwardly direction from the inner portion side towards the outer peripheral edge, wherein an exposed portion of the outer margin having the thickness that decreases in the outwardly direction is tissue infiltratable.

2. The implantable prosthesis of claim 1, wherein the inner portion is tissue infiltratable.

3. The implantable prosthesis of claim 1, wherein the thickness of the outer margin decreases progressively from the inner portion side towards the outer peripheral edge.

4. The implantable prosthesis of claim 3, wherein the thickness of the outer margin decreases progressively from the inner portion side to the outer peripheral edge.

5. The implantable prosthesis of claim 1, wherein the thickness of the outer margin decreases in a stepped fashion from the inner portion side towards the outer peripheral edge.

6. The implantable prosthesis of 5, where the thickness of the outer margin decreases in a stepped fashion from the inner portion side to the outer peripheral edge.

7. The implantable prosthesis of claim 1, wherein the outer margin has a non-uniform thickness.

8. The implantable prosthesis of claim 7, wherein the outer peripheral edge includes first and second spaced peripheral edge regions, wherein a thickness of the first peripheral edge region differs from a thickness of the second peripheral edge region.

9. The implantable prosthesis of claim 1, wherein the outer margin includes a knitted fabric.

10. The implantable prosthesis of claim 9, wherein:
the inner portion includes a knitted fabric with a first pore size;
the knitted fabric outer margin includes a second pore size; and
the second pore size is greater than the first pore size.

11. The implantable prosthesis of claim 10, wherein the body further comprises at least one intermediate portion disposed between the inner portion and the outer margin, wherein the at least one intermediate portion includes a knitted fabric with a third pore size, the third pore size being greater than the first pore size but less than the second pore size.

12. The implantable prosthesis of claim 9, wherein the knitted fabric is formed of at least one of monofilament or multifilament fibers.

13. The implantable prosthesis of claim 12, wherein:
the inner portion is formed from monofilament or multifilament fibers with a first diameter; and
the knitted outer margin is formed from monofilament or multifilament fibers with a second diameter; and
the first diameter is greater than the second diameter.

14. The implantable prosthesis of claim 13, wherein the body further comprises at least one intermediate portion disposed between the inner portion and the outer margin, the at least one intermediate portion formed from monofilament or multifilament fibers with a third diameter, the third diameter being greater than the second diameter but less than the first diameter.

15. The implantable prosthesis of claim 9, wherein the inner portion includes a knitted fabric formed with a first knit pattern and the outer margin includes the knitted fabric formed with a second knit pattern, the first knit pattern being different than the second knit pattern.

16. The implantable prosthesis of claim 15, wherein the body further comprises at least one intermediate portion disposed between the inner portion and the outer margin, the at least one intermediate portion including a knitted fabric formed with a third knit pattern, the third knit pattern being different from the first and second knit patterns.

17. The implantable prosthesis of claim 9, wherein the outer margin includes a first region having a knitted fabric formed with a first knit pattern and a second region having a knitted fabric formed with a second knit pattern, the first knit pattern being different than the second knit pattern.

18. The implantable prosthesis of claim 1, wherein the outer margin is more flexible than the inner region.

19. The implantable prosthesis of claim 1, wherein the inner portion is formed of a first fabric having a first fabric construction and the outer margin is formed of a second fabric having a second fabric construction, the first fabric construction being different from the second fabric construction.

20. The implantable prosthesis of claim 1, wherein the outer margin includes one or more sheets of prosthetic repair fabric.

21. The implantable prosthesis of claim 1, wherein the outer margin comprises:
a first tissue infiltratable layer having a first outer peripheral edge; and
a second tissue infiltratable layer having a second outer peripheral edge, the second layer being positioned on the first layer such that the second peripheral edge is disposed inwardly of the first peripheral edge.

22. The implantable prosthesis of claim 21, wherein the outer margin comprises first and second thicknesses, the first thickness including a thickness of the first tissue infiltratable layer and the second thickness including a sum of the thickness of the first tissue infiltratable layer and a thickness of the second tissue infiltratable layer.

23. The implantable prosthesis of claim 22, wherein the thickness of the first tissue infiltratable layer is the same as the thickness of the second tissue infiltratable layer.

24. The implantable prosthesis of claim 22, wherein the thicknesses of the first and second tissue infiltratable layers are different.

25. The implantable prosthesis of claim 21, wherein the first and second tissue infiltratable layers have the same shape.

26. The implantable prosthesis of claim 21, wherein the outer margin further comprises at least one additional tissue infiltratable layer, wherein the at least one additional tissue infiltratable layer is positioned on the second tissue infiltratable layer such that an outer peripheral edge of the at least one additional layer is disposed inwardly of the second outer peripheral edge.

27. The implantable prosthesis of claim 26, wherein the outer margin comprises first, second and third thicknesses, wherein:
the first thickness includes a thickness of the first tissue infiltratable layer;
the second thickness includes a sum of the thickness of the first tissue infiltratable layer and a thickness of the second tissue infiltratable layer; and
the third thickness includes a sum of the thicknesses of the first and second tissue infiltratable layers and a thickness of the at least one additional tissue infiltratable layer.

28. A method of repairing a soft tissue defect with an implantable prosthesis, the method comprising:
covering or plugging the soft tissue defect with the implantable prosthesis, the prosthesis including a body having an inner portion and an outer margin extending outwardly beyond the inner portion, the outer margin having an inner portion side and an outer peripheral edge, wherein the outer margin comprises a tissue infiltratable portion having a thickness that decreases in an outwardly direction from the inner portion side towards the outer peripheral edge, wherein an exposed portion of the outer margin having the thickness that decreases in the outwardly direction is tissue infiltratable.

29. The method of claim 28, wherein covering or plugging the soft tissue defect includes covering or plugging the soft tissue defect with the inner portion.

30. The method of claim 29, wherein covering or plugging the soft tissue defect with the inner portion includes covering or plugging the soft tissue defect such that the inner portion extends between about 3 cm and 5 cm beyond the defect.

31. The method of claim 28, wherein covering or plugging the soft tissue defect includes covering or plugging the soft tissue defect with a tissue infiltratable inner portion.

32. The method of claim 31, wherein covering or plugging the soft tissue defect with at least a portion of the outer margin comprises covering the soft tissue defect with the at least a portion of the outer margin having a thickness that decreases in a stepped fashion from the inner portion side towards the outer peripheral edge.

33. The method of claim 28, wherein covering or plugging the soft tissue defect includes covering or plugging the soft tissue defect with the inner portion and at least a portion of the outer margin.

34. The method of claim 33, wherein covering or plugging the soft tissue defect with at least a part of the outer margin comprises covering the soft tissue defect with the at least a portion of the outer margin having a thickness that decreases progressively from the inner portion side towards the outer peripheral edge.

\* \* \* \* \*